(12) United States Patent
Zhou et al.

(10) Patent No.: US 10,974,981 B2
(45) Date of Patent: Apr. 13, 2021

(54) METHOD FOR REDUCING POLLUTANT DISCHARGE IN PHENOL AND ACETONE PRODUCTION

(71) Applicant: Chinese Research Academy of Environmental Sciences, Beijing (CN)

(72) Inventors: Yuexi Zhou, Beijing (CN); Yudong Song, Beijing (CN)

(73) Assignee: Chinese Research Academy of Environmental Sciences, Beijing (CN)

( * ) Notice: Subject to any disclaimer, the term of this patent is extended or adjusted under 35 U.S.C. 154(b) by 0 days.

(21) Appl. No.: 16/088,942

(22) PCT Filed: Mar. 31, 2017

(86) PCT No.: PCT/CN2017/078960
§ 371 (c)(1),
(2) Date: Jul. 13, 2020

(87) PCT Pub. No.: WO2017/167262
PCT Pub. Date: Oct. 5, 2017

(65) Prior Publication Data
US 2020/0346959 A1    Nov. 5, 2020

(30) Foreign Application Priority Data

Apr. 1, 2016 (CN) .......................... 201610203587.5

(51) Int. Cl.
*C02F 9/00* (2006.01)
*C02F 1/26* (2006.01)
(Continued)

(52) U.S. Cl.
CPC ................ *C02F 9/00* (2013.01); *C07C 37/88* (2013.01); *C07C 45/80* (2013.01); *C02F 1/26* (2013.01);
(Continued)

(58) Field of Classification Search
CPC ......... C07C 39/04; C07C 49/08; C07C 37/74; C07C 37/685; C07C 409/10; C02F 1/725;
(Continued)

(56) References Cited

U.S. PATENT DOCUMENTS 3,963,610 A * 6/1976 Hauschulz ................ C02F 1/26
210/638
5,061,343 A * 10/1991 Azarniouch ....... D21C 11/0042
162/16
(Continued)

FOREIGN PATENT DOCUMENTS

CN    101654316 A    2/2010
CN    102908916 A    2/2013
(Continued)

OTHER PUBLICATIONS

Chinese Office Action—Application No. 201610203587.5—dated Feb. 13, 2018.
(Continued)

*Primary Examiner* — Claire A Norris
(74) *Attorney, Agent, or Firm* — Amster, Rothstein & Ebenstein LLP

(57) ABSTRACT

A method for reducing pollutant discharge in phenol acetone production, comprising at least one of the following steps: (A) collecting phenolic wastewater generated by a phenol-acetone plant, adjusting the pH value to acidic, and performing extraction and recovery on the phenols in wastewater using cumene as an extracting agent; (B) reducing the acetone content in the wastewater from a column bottom by means of optimizing the process of an acetone refining column; (C) treating the wastewater from the column bottom of the acetone refining column by using a permselective membrane, and recovering alkali; (D) neutralizing the wastewater obtained from step (C), mixing the neutralized wastewater with a condensation liquid at the top of a cumene (Continued)

oxidation column, and carrying out a detoxification treatment; (E) carrying out an oil separation treatment on total discharged wastewater from the phenol-acetone plant, and recovering organic matters comprising hydrocarbons; and (F) carrying out a biological treatment, a coagulation sedimentation treatment and a reinforced degradation treatment on the wastewater after undergoing the oil separation treatment. The method has at least one of characteristics of being capable of recovering resources, increasing product yield, reducing pollutant discharge, having low cost in wastewater treatment, and having stable quality for water output.

8 Claims, 5 Drawing Sheets

(51) Int. Cl.
| | | |
|---|---|---|
| *C07C 37/88* | (2006.01) | |
| *C07C 45/80* | (2006.01) | |
| *C02F 1/28* | (2006.01) | |
| *C02F 1/40* | (2006.01) | |
| *C02F 1/44* | (2006.01) | |
| *C02F 1/52* | (2006.01) | |
| *C02F 1/56* | (2006.01) | |
| *C02F 1/66* | (2006.01) | |
| *C02F 1/70* | (2006.01) | |
| *C02F 1/72* | (2006.01) | |
| *C02F 1/78* | (2006.01) | |
| *C02F 3/12* | (2006.01) | |
| *C02F 101/34* | (2006.01) | |
| *C02F 103/36* | (2006.01) | |

(52) U.S. Cl.
CPC ............... *C02F 1/283* (2013.01); *C02F 1/40* (2013.01); *C02F 1/44* (2013.01); *C02F 1/5245* (2013.01); *C02F 1/56* (2013.01); *C02F 1/66* (2013.01); *C02F 1/705* (2013.01); *C02F 1/722* (2013.01); *C02F 1/725* (2013.01); *C02F 1/78* (2013.01); *C02F 3/12* (2013.01); *C02F 2101/345* (2013.01); *C02F 2103/36* (2013.01)

(58) Field of Classification Search
CPC .. C02F 1/722; C02F 1/78; C02F 1/001; C02F 1/04; C02F 2101/345
USPC ........ 568/749, 810; 210/634, 760, 763, 758, 210/759
See application file for complete search history.

(56) References Cited

U.S. PATENT DOCUMENTS

| | | | |
|---|---|---|---|
| 2008/0281129 A1* | 11/2008 | Palmer | ................... C07C 37/08 568/724 |
| 2010/0140075 A1* | 6/2010 | Nelson | ................... C07C 45/82 203/31 |

FOREIGN PATENT DOCUMENTS

| | | |
|---|---|---|
| CN | 102992961 A | 3/2013 |
| CN | 103145286 A | 6/2013 |
| CN | 104355501 A | 2/2015 |
| CN | 105819588 A | 8/2016 |
| DE | 2235493 A1 | 1/1974 |
| DE | 19837723 A1 | 2/2000 |

OTHER PUBLICATIONS

Chinese Notice of Allowance—Application No. 201610203587.5—dated Sep. 13, 2018.
German Office Action dated Aug. 6, 2019 in connection with German Application No. 11 2017 001 666.5.
Haihong, et al. "Technical Revamping of the Acetone Distillation Tower in Cresol Plant"—Chemical Industry Engineering, vol. 14, No. 3—Aug. 8, 1997 (pp. 56-59).

* cited by examiner

METHOD FOR REDUCING POLLUTANT DISCHARGE IN PHENOL AND ACETONE PRODUCTION

TECHNICAL FIELD

The present application relates to a method for reducing and controlling wastewater and pollutants from phenol and acetone production plants during resources recovery therefrom, which is also a method for reducing pollutant discharge in the process of producing phenol and acetone.

BACKGROUND

Phenol and acetone are important basic chemical raw materials. Currently, the cumene method is the dominant process for producing phenol and acetone. The process uses propylene and benzene as the main raw materials to produce cumene which then is oxidized to form cumene hydroperoxide. Cumene hydroperoxide is thereafter decomposed under acidic heating conditions to produce phenol and acetone, which is subjected to rectification and refining to yield phenol and acetone products.

The phenol and acetone production has many procedures and wastewater discharge are involved in lots of the procedures. Most technologies for treating the wastewater from the phenol and acetone plant in the prior art are focused on the final treatment of the mixed wastewater from the equipment. While, few technologies pay attention to reducing the pollutant discharge in the midst of the production. As a result, the mixed wastewater from the phenol and acetone plant has high concentration of pollutants with high toxicity. The treatment of the wastewater is difficult and the cost for the treatment is high. Furthermore, the effluent after treatment is difficult to meet the standards.

SUMMARY OF THE INVENTION

The present application is to provide a method for reducing and controlling the wastewater and the pollutant from the phenol and acetone production plants during resources recovery. It can at least recover the resources from wastewater during the production of phenol and acetone, reduce the concentration of the pollutants and the toxicity of wastewater, and/or decrease the difficulty for treating the wastewater.

The conventional cumene method for producing phenol and acetone includes the following steps:

(1) Hydrocarbonylation section: Raw materials of benzene and propylene are reacted in the alkylation reactor to produce cumene, and the obtained cumene is subjected to rectification to obtain high-purity cumene for use in the oxidation section.

(2) Oxidizing, extracting, concentrating and decomposing section: After alkali washing, cumene is oxidized by air in the oxidation reactor to produce cumene hydroperoxide, then extracted and concentrated, and finally decomposed under the action of sulfuric acid to produce crude products (mainly a mixture of phenol, acetone, cumene and α-methylstyrene (AMS)). This section produces phenol containing wastewater.

(3) Neutralization section: Hexamethylene diamine is added to the crude product to neutralize the sulfuric acid, then the product is sent to the rectification section.

(4) Rectification section: By passing six rectification columns including crude acetone column, acetone refining column, cumene rectification column, tar column, AMS column and refined phenol column, finished products of phenol and acetone as well as by-products of AMS, cumene and tar are obtained. The crude acetone is a feed overhead of the crude acetone column, which enters the acetone refining column for refining and the acetone product is obtained by side cut-draw. In the acetone refining column, in order to ensure the quality of the acetone product, an alkali liquor such as NaOH solution is added to the column to remove aldehyde. The port for adding NaOH solution is located above the port for adding the feed of crude acetone. A portion of the overhead condensate is refluxed (aldehyde removal reflux) to the stripping section to further enhance the aldehyde removal effect. Other overhead condensate is refluxed to the top plates of the acetone refining column (overhead reflux). After separating between oil and water, the heavy components of the acetone refining column are discharged as alkaline organic wastewater with high concentrations. The condensate in the vacuum system of the six rectification columns is also discharged as wastewater.

According to one aspect of the present application, the present application provides a method for reducing the pollutant discharge in the production of phenol and acetone, which includes at least one of the following steps:

(A) collecting phenols containing wastewater produced by a phenol and acetone production plant, adjusting the pH to acidic, and performing extraction and recovery of the phenols in the wastewater by using cumene as an extracting agent;

(B) reducing the content of acetone in the wastewater from a column bottom by optimizing the process of an acetone refining column;

(C) treating the wastewater from the column bottom of the acetone refining column by using a permselective membrane, and recovering alkali;

(D) neutralizing the wastewater obtained from step (C), then mixing the neutralized wastewater with an overhead condensate of a cumene oxidation column, and carrying out a detoxification treatment;

(E) carrying out an oil separation treatment on the total discharged wastewater from the phenol and acetone production plant, and recovering the organic matters including hydrocarbons; and (F) subjecting the wastewater obtained from step (E) to at least one of the treatments selected from the group consisting of a biological treatment, a coagulation sedimentation treatment and a reinforced degradation treatment.

According to some embodiments, the phenol containing wastewater in step (A) includes wastewater coming from one of the following steps for producing phenol and acetone: oxidation, extraction and concentration of cumene, decomposition and rectification of cumene hydroperoxide.

In step (A) of the method of the present application, the wastewater usually contains 0.1 wt % to 2 wt % phenol, the pH of the wastewater can be adjusted to be acidic (pH ranging from 4.5 to 5.5) and the temperature can be 10 to 60° C. In the extraction column, the phenols in the wastewater are extracted by using cumene as the extracting agent. The volume ratio of cumene to the wastewater is from 5:1 to 20:1. The obtained cumene solution rich in phenols can be regenerated by a 10 wt % to 20 wt % NaOH solution, wherein the volume of the NaOH solution is 0.1 to 0.6 times of wastewater.

The cumene after dephenolization is recycled as the extracting agent for extracting wastewater. Sodium phenolate solution produced by regeneration is acidized by sulfuric acid. After passing a desalination separator (a two-stage desalination separator), the organic phase containing phenols enters into a neutralization section for recovering phenol and the aqueous phase is subjected to extraction treatment.

In step (A), the recovery rate of phenol in the wastewater can reach more than 99%. When the content of acetone in the recycled cumene reaches more than 10%, the cumene shall be replaced.

According to some embodiments, step (B) includes at least one of the following means for optimizing the process of the acetone refining column and decreasing the acetone content in the wastewater of a column bottom: (1) installing packing in the liquid on the plates below the alkali liquor feed inlet; (2) separately controlling the acetone refining column and decreasing the overhead vacuum by 5 to 20 kPa; (3) reducing the flow of overhead reflux for aldehyde removal by 10% to 50%; (4) increasing the stripping section below the overhead reflux plates for aldehyde removal by 1 to 2 theoretical plates. After this treatment, the acetone content in the wastewater can be decreased to 0.01 wt % to 0.1 wt %

In step (B), the packing is installed in the liquid on the plates, wherein the packing is a ringlike or structured packing.

In step (B), the overhead reflux for aldehyde removal is a reflux wherein the stream overhead is condensed firstly, then refluxed to the stripping section (below the feed inlet).

In step (C), the wastewater of the column bottom of acetone refining column is treated by using a permselective membrane. The wastewater of the column bottom of acetone refining column is cooled (via heat exchange), for example, to 20 to 30° C., and subjected to oil separation and activated carbon adsorption treatments, then circulated through a compartment formed by the permselective membrane. Meanwhile, permselective membrane forms the same compartment on the other side for circulating deionized water. NaOH in the wastewater passes through the permselective membrane and enters into the deionized water side to achieve alkali recovery. The recovery rate is more than 60%.

The permselective membrane is resistant to acetone and benzenes solvents and enables selective permeation of NaOH.

According to some embodiments, the permselective membrane used in the method according to the present application includes, but is not limited to, a perfluorinated cation exchange membrane.

In step (D), after recovering alkali in step (C), the wastewater of the column bottom of the acetone refining column is neutralized, followed by mixing with an overhead condensate of a cumene oxidation column, and subjected to a detoxification treatment.

In some embodiments, in step (D), after recovering alkali in step (C), the wastewater of the column bottom of the acetone refining column is neutralized, followed by mixing with an overhead condensate of a cumene oxidation column. The pH of the wastewater is controlled to be 3 to 5 and the temperature is 20 to 60° C. A reduction catalyst is added in an amount of 5-30 mg/L for reacting, for example, for 5 to 10 min. The toxicity of wastewater to the activated sludge microorganisms is reduced. The inhibition rate of oxygen utilization of the activated sludge is reduced to less than 20%. The conversion rate of the non-degradable organic matters in the wastewater from the column bottom of acetone refining column is more than 70 wt %, for example, 70 to 95%.

In some embodiments, in step (D), the reductive catalyst is a divalent iron ion, a cobalt ion or a manganese ion.

The method according to the present application further includes a step (E), wherein the total discharged water from the phenol and acetone plant is subjected to an oil separation treatment.

According to some embodiments, in step (E), the wastewater enters an oil separation tank with inclined plates for separating oil from water. The oil layer its is discharged from the upper part of the oil separation tank and the organic matters such as hydrocarbons are recovered. The oil is removed by more than 90%. After this treatment, the wastewater is discharged from the lower part of the oil separation tank for subsequent treatment.

The method according to the present application also includes step (F), wherein after the oil separation treatment, the wastewater is subjected to at least one of the treatments selected from the group consisting of a biological treatment, a coagulation sedimentation treatment and a reinforced degradation treatment.

According to some embodiments, in step (F), the biological treatment is an aerobic biological treatment. The microorganism growth of the biological treatment is a suspension growth or a suspension growth coexisted with an attachment growth. The reinforced degradation treatment is performed by using ozone or $H_2O_2$ as oxidants. After the treatment of step (F), the COD of the effluent can be decreased to less than 50 mg/L wherein phenol and acetone are not detectable.

According to some embodiments, when ozone is used as an oxidant in the reinforced degradation treatment, the ozone column is filled with an aluminum-based or copper-based supported catalyst, the temperature is 20 to 40° C., the pH of the wastewater is 4 to 10, and the amount of the ozone is 50 to 300 mg/L. When $H_2O_2$ is used as an oxidant in the reinforced degradation treatment, the catalyst is a divalent iron ion, the pH of the wastewater is adjusted to 3 to 6, the amount of the divalent iron ion is 50 to 200 mg/L and the amount of $H_2O_2$ is 100 to 330 mg/L. After reaction under stirring and mixing, the pH of the wastewater is adjusted to 8 for the coagulation sedimentation treatment.

According to some embodiments, the above coagulation sedimentation treatment may use metal salts selected from the group consisting of aluminum sulfate, polyaluminum chloride, ferric chloride and a combination thereof as a coagulant, and polyacrylamide as a flocculant. The temperature is 20-40° C., pH is 6-9 and sedimentation is carried out for 30 to 60 min.

The method for reducing the pollutants from the phenol and acetone plant according to the present application has at least one of the following advantages:

(1) Through the optimization of the production process, the method according to the present application achieves the recovery of phenol, acetone and alkali from the wastewater at the main discharge sections of phenol, acetone and NaOH, improves the utilization of raw materials and the yield of the products, reduces the concentrations of phenol, acetone and alkali in wastewater and decreases the difficulty for treating the wastewater.

(2) Treating the wastewater from various sections respectively according to its characteristics. While ensuring the efficiency of pollutants removal, the cost for treating the wastewater is reduced. The overhead condensate of the cumene oxidation column contains oxidizing substances, and the activated sludge has high toxicity, which will adversely affect the operational stability of the subsequent biological treatment system. The wastewater of the column bottom of the acetone refining column contains high concentration of alkali, which need huge acid consumption in the subsequent neutralization treatment. Moreover, the content of salts in the neutralized wastewater is high and the wastewater is difficult to handle. Additionally, the wastewater contains high concentration of non-degradable organic matters. Regarding the above two types of wastewater, according to the method of the present application, firstly, the alkali in the wastewater of the column bottom of the acetone refining column is recovered, then the wastewater is neutralized, followed by mixing with the overhead condensate of the cumene oxidation column. By using the oxidizing substances in the wastewater as oxidants, the non-degradable organic matters are converted under the activity of reductive catalyst. Based on the method according to the present application, on the one hand, the toxicity of the overhead condensate of the cumene oxidation column is reduced. On the other hand, the biodegradability of the wastewater is improved.

(3) The effluent of the treated wastewater contains low levels of pollutants. After oil separation treatment, the wastewater is subjected to at least one of the treatments selected from the group consisting of a biological treatment, a coagulation sedimentation treatment and a reinforced degradation treatment, which can decrease the concentration of the pollutants to a very low level.

(4) The present application makes improvement on the main procedures of the current cumene method, which is suitable for the transformation of existing production facilities. With a small investment, significant effects on the resource recovery and pollutant reduction can be achieved.

The method for reducing the pollutants discharge in the production of phenol and acetone according to the present application will be further described below with reference to the accompanying drawings and specific embodiments.

DETAILED DESCRIPTION OF EMBODIMENTS

Example 1

Figure 1:
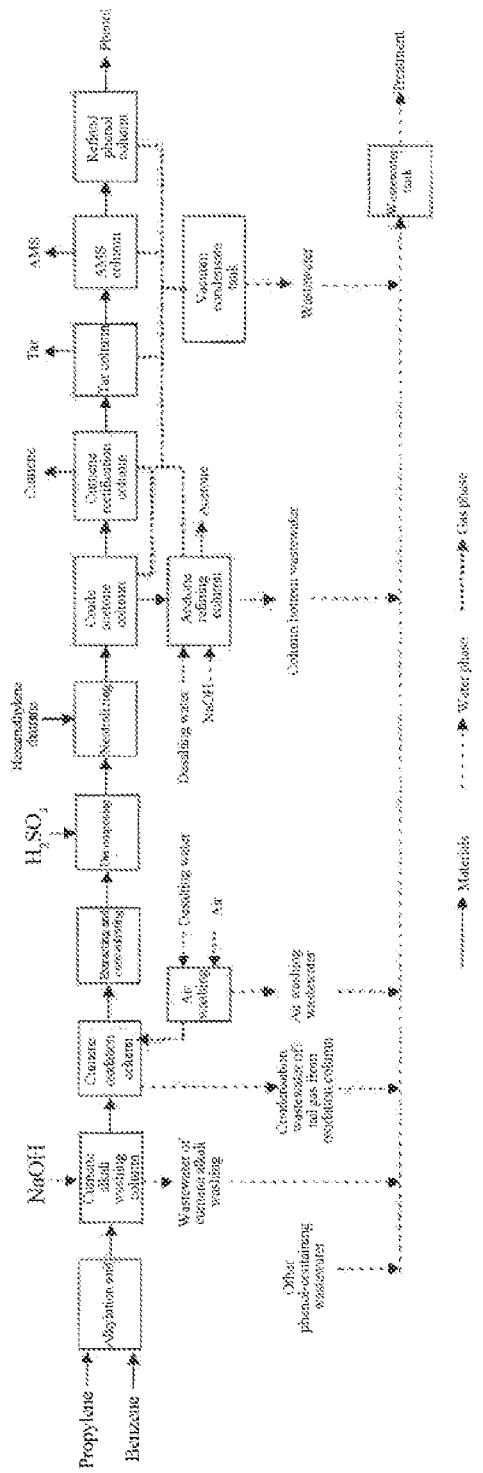
FIG. 1 shows the process for producing phenol and acetone based on traditional cumene method.
Figure 2:
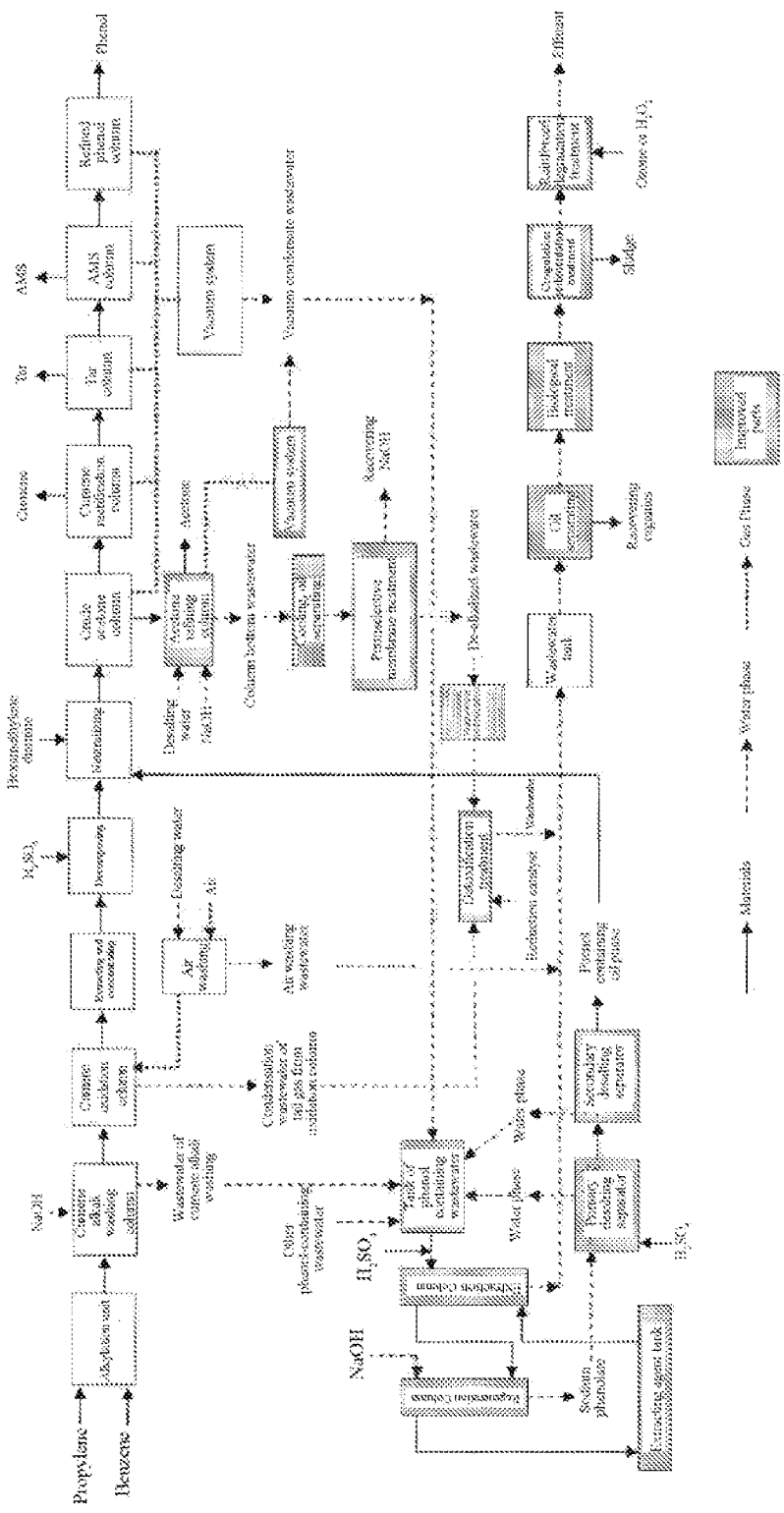
FIG. 2 shows an improved process for producing phenol and acetone based on traditional cumene method, according to the present application.

Phenol and acetone were prepared by using the traditional cumene method (see FIG. 1). The COD of the total discharged wastewater was up to 4000-8000 mg/L.

Figure 3:
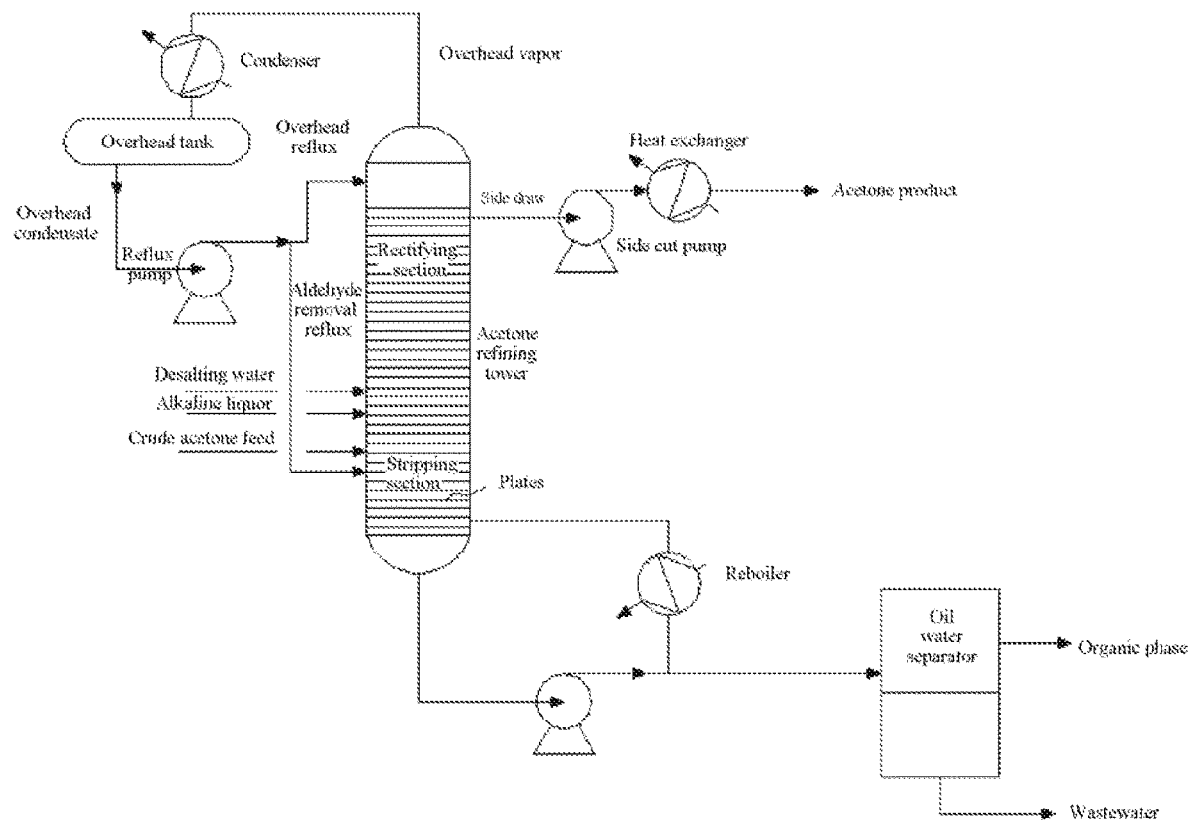
FIG. 3 shows a schematic diagram of an acetone refining column.
Figure 5:
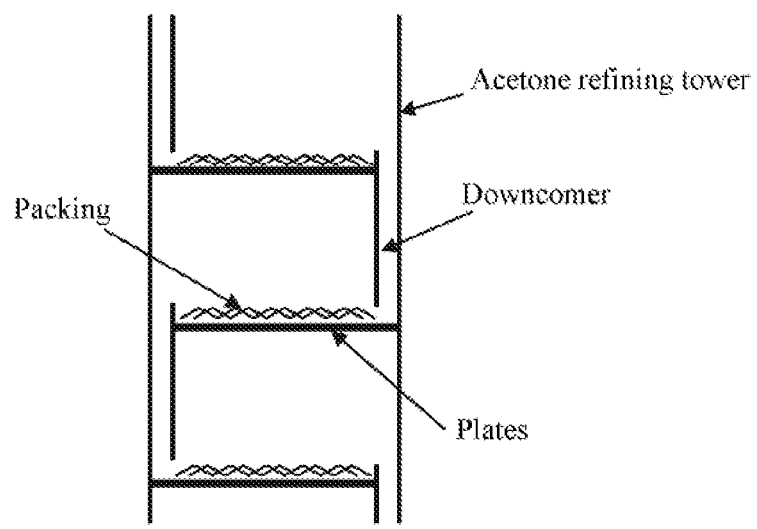
FIG. 5 is a schematic diagram of the packing installed in the liquid layer on the plates of the acetone refining column.

The method according to the present application modified the traditional cumene method and the facilities thereof by at least one of the following means:

(1) A separate vacuum system was installed in the acetone refining column, which decreased the column top pressure by 15 kPa, A thin layer of structured packing was installed in the liquid layer on the plates below the alkali liquor feed inlet (see FIG. 3 and FIG. 5). The overhead refluxes to column top and for aldehyde removal were decreased by 25%. While ensuring the product quality of the side draw, the steam consumption of the column bottom of the acetone refining column was reduced by 20% and the content of acetone from the column bottom was reduced from 2200 mg/L to 520 mg/L.

(2) After collecting the phenol containing wastewater in the phenol containing wastewater tank, the pH was adjusted to 5 with sulfuric acid, cumene was used as an extracting agent and the flow was 20 times of the wastewater. In the extraction column, phenol in the wastewater was extracted. The obtained cumene rich in phenol was regenerated with a 15 wt % NaOH solution in amount of 0.5 times of the wastewater. After dephenolization and regeneration, the cumene was recycled as an extracting agent for extracting wastewater. Sodium phenolate solution obtained by regeneration was acidized by sulfuric acid. After passing a two-stage desalination separator, the organic phase containing phenols entered a neutralization section for recycling phenol and the aqueous phase was subjected to extraction treatment. The concentration of the phenol in the wastewater was decreased from 5000 mg/L to 50 mg/L.

Figure 4:
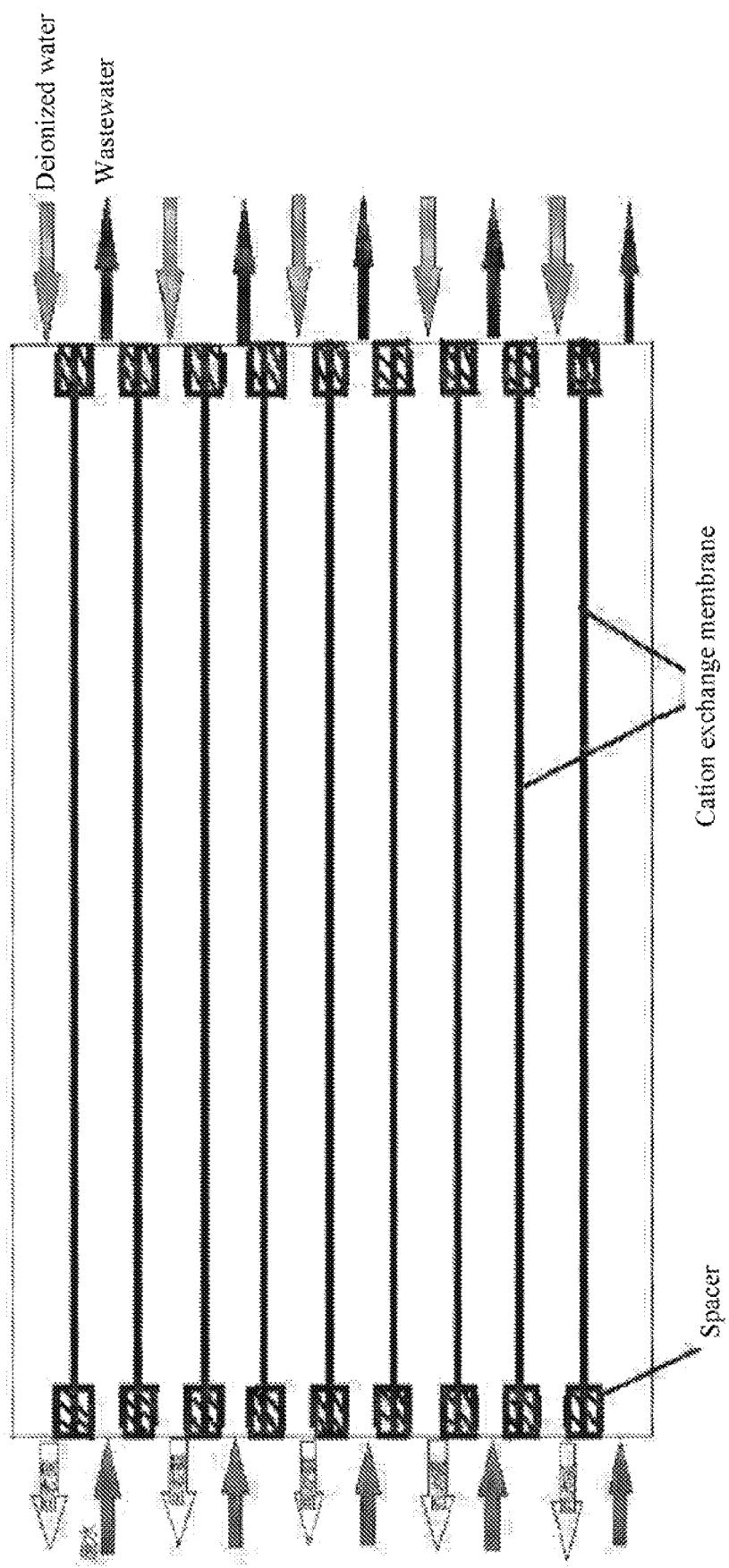
FIG. 4 shows a schematic diagram of a compartment formed by a permselective membrane (countercurrent operation).

(3) The wastewater of the column bottom of acetone refining column was cooled (via heat exchange) and subjected to oil separation treatment, then circulated through a compartment formed by a perfluorinated cation exchange membrane. The ion exchange membrane constituted the same compartment on the other side for circulating deionized water. NaOH in the wastewater passed through the ion exchange membrane and entered the deionized water side to achieve alkali recovery, see FIG. 4. By this step, the concentration of the alkali in the wastewater can be reduced from 2 mol/L, to 0.5 mol/L. The alkali solution recovered can be used for neutralizing acidic wastewater.

(4) After recovering alkali, the wastewater of the column bottom of the acetone refining column was neutralized, followed by mixing with an overhead condensate of a cumene oxidation column. 10 mg/L $Mn^{2+}$ was added as a catalyst and the reaction was carried out at pH of 5, at a temperature of 30° C. for 10 min. The inhibition rate of the activated sludge OUR was reduced to less than 20%. The non-degradable organic matters in the wastewater of the column bottom of acetone refining column was removed by more than 70 wt/o.

(5) After being treated by all the above means (1)-(4), the total discharged wastewater of the plant was subjected to oil separation treatment. At this time, the COD of the treated wastewater was 1800 mg/L. Then the wastewater was subjected to aerobic activated sludge treatment, and the COD was removed by 88%. Aluminum sulfate and polyacrylamide (PAM) were used as coagulant and coagulant aid, respectively, for coagulation and sedimentation treatment. Ozone was then used as an oxidant for a reinforced degradation treatment. The ozone column was filled with a copper-based supported catalyst, wherein ozone was 200 mg/L in amount. The COD of the effluent treated was below 50 mg/L, and phenol and acetone were not detectable.

Example 2

The method according to the present application modified the traditional cumene method and the facilities thereof by at least one of the following means:

The modifications of (1) to (4) were the same as in Example 1.

(5) The total discharged wastewater of the plant was subjected to oil separation treatment. At this time, the COD of the treated wastewater was 1800 mg/L. Then the wastewater was subjected to aerobic biological fluidized bed treatment, and the COD was removed by 87%. Polyaluminium chloride (PAC) and PAM were used as coagulant and coagulant aid, respectively, for coagulation and sedimentation treatment. $H_2O_2$ was then used as an oxidant for a reinforced degradation treatment, wherein $H_2O_2$ was added in amount of 250 mg/L. Ferrous ions were used as the catalyst in amount of 50 mg/L. The COD of the effluent treated was below 50 mg/L, and phenol and acetone were not detectable.

The above embodiments are presented only for illustrating the preferred embodiments of the present application, which are not intended to limit the scope of the present application. Without departing from the spirit of the present application, those skilled in the art can make various modifications and improvements to the technical solutions of the present application, which should fall within the protection scope defined by the claims of the present application.

We claim:

1. A method for reducing the pollutant discharge in the production of phenol and acetone
  by conventional cumene method including the following steps: (1) hydrocarbonylation section; (2) oxidizing, extracting, concentrating and decomposing section in which section, after alkali washing, cumene is oxidized by air in an oxidation reactor to produce cumene hydroperoxide, then extracted and concentrated, and finally decomposed under action of sulfuric acid to produce crude products, which section produces phenols containing wastewater; (3) neutralization section; and (4) rectification section in which finished products of phenol and acetone as well as by-products of AMS, cumene and tar are obtained by passing six rectification columns including crude acetone column, acetone refining column, cumene rectification column, tar column, AMS column and refined phenol column; and the condensate in a vacuum system of the six rectification columns is also discharged as wastewater;
  comprising the following steps:
  (A) collecting the phenols containing wastewater, adjusting the pH to acidic, and performing extraction and recovery of the phenols in the wastewater by using cumene as an extracting agent;
  (B) reducing the content of acetone in the wastewater from column bottom by optimizing the process of acetone refining column by at least one of the following means: (1) installing ring like packing or structured packing in the liquid layer on the plates below alkali liquor feed inlet of the acetone refining column; (2) separately controlling the acetone refining column and decreasing column top pressure by 5 to 20 kPa; (3) reducing overhead reflux for aldehyde removal by 10% to 50%; (4) increasing stripping section below overhead reflux plates for aldehyde removal by 1 to 2 theoretical plates; wherein after the treatment of step (B), the content of acetone in the wastewater is decreased to 0.01 wt % to 0.1 wt %;
  (C) treating the wastewater from the column bottom of the acetone refining column by using a permselective membrane, and recovering alkali;
  (D) neutralizing the wastewater obtained from step (C), and mixing the neutralized wastewater with overhead condensate of cumene oxidation column, and then carrying out detoxification treatment;
  (E) carrying out oil separation treatment on the discharge from the above four steps, and recovering organic matters including hydrocarbons; and
  (F) subjecting the wastewater, after undergoing the oil separation treatment, to at least one of the treatments selected from the group consisting of a biological treatment, a coagulation sedimentation treatment and a reinforced degradation treatment,
  wherein the detoxification treatment in step (D) comprises: mixing the wastewater treated in step (C) with the overhead condensate of the cumene oxidation column, controlling the pH of the wastewater ranging from 3 to 5 and the temperature being 20 to 60° C., adding 5-30 mg/L reductive catalyst, to reduce the toxicity of the wastewater against activated sludge microorganisms, and reduce the inhibition rate of oxygen utilization of the activated sludge to less than 20%, and obtain a conversion rate of non-degradable organic matters in the wastewater from the column bottom of acetone refining column amounting to more than 70 wt %.

2. The method according to claim 1, wherein in step (A), adjusting the pH of the wastewater to acidic with a pH ranging from 4.5 to 5.5, extracting phenols from the wastewater by using cumene as an extracting agent with a volume ratio of cumene to wastewater ranging from 5:1 to 20:1, regenerating the cumene rich in phenols by using a 10 wt % to 20 wt % NaOH solution with the volume of the NaOH solution being 0.1 to 0.6 times of the wastewater and recycling the cumene after dephenolization as the extracting agent in the treatment of wastewater.

3. The method according to claim 1, wherein in step (C), the treatment by permselective membrane includes cooling the wastewater of the column bottom of acetone refining column first, subjecting it to oil separation and activated carbon adsorption treatments, then circulating through a compartment formed by permselective membrane; and permselective membrane forms the same compartments on the other side for circulating deionized water; NaOH in the wastewater passes through the permselective membrane and enters the deionized water side to achieve alkali recovery.

4. The method according to claim 3, wherein the permselective membrane is resistant to solvents of acetone and benzenes and enables selective permeation of NaOH.

5. The method according to claim 1, wherein the reductive catalyst is a divalent iron ion, a cobalt ion or a manganese ion.

6. The method according to claim 1, wherein in step (F), the biological treatment is an aerobic biological treatment, and the microorganism growth is a suspension growth or a suspension growth coexisted with an attachment growth; or the reinforced degradation treatment is performed by using ozone or $H_2O_2$ as oxidants.

7. The method according to claim 6, wherein ozone is used as an oxidant to perform the reinforced degradation treatment, the ozone column is filled with an aluminum-based or copper-based supported catalyst, the temperature is 20 to 40° C., the pH of the wastewater is 4 to 10, and ozone is added in an amount of 50 to 300 mg/L.

8. The method according to claim 6, wherein $H_2O_2$ is used as an oxidant to perform the reinforced degradation treatment, the catalyst is divalent iron ion, the pH of the wastewater is adjusted to 3 to 6, the divalent iron ion is added in an amount of 5 to 200 mg/L, and $H_2O_2$ is added in an amount of 100 to 330 mg/L.

\* \* \* \* \*